(12) United States Patent
Shur

(10) Patent No.: US 9,214,317 B2
(45) Date of Patent: Dec. 15, 2015

(54) SYSTEM AND METHOD OF SEM OVERLAY METROLOGY

(71) Applicant: KLA-Tencor Corporation, Milpitas, CA (US)

(72) Inventor: Dmitry Shur, Holon (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/290,556

(22) Filed: May 29, 2014

(65) Prior Publication Data

US 2014/0353498 A1    Dec. 4, 2014

Related U.S. Application Data

(60) Provisional application No. 61/830,927, filed on Jun. 4, 2013.

(51) Int. Cl.
  *H01J 37/26* (2006.01)
  *H01J 37/28* (2006.01)
  *G01N 21/66* (2006.01)
  (Continued)

(52) U.S. Cl.
  CPC .............. *H01J 37/26* (2013.01); *G01N 21/66* (2013.01); *G06T 7/0004* (2013.01); *H01J 37/28* (2013.01); *H01L 22/34* (2013.01); *H01J 2237/2809* (2013.01); *H01J 2237/2814* (2013.01); *H01J 2237/2817* (2013.01)

(58) Field of Classification Search
  CPC ......... G06T 7/00; G06T 7/001; G06T 7/0004; G06T 7/0028; G01N 21/9501; G01N 21/95607; G01N 21/66; G01N 21/8851; G01N 21/956; G01N 23/04; G01N 23/2273; H01J 37/26; H01J 37/28; H01J 37/3175; H01J 37/3177; H01J 40/14; H01L 22/34; H01L 22/14; H01L 22/20
  USPC ........ 250/306, 307, 310, 492.2, 492.3, 252.1, 250/396 R, 491.1, 492.1, 492.22, 559.45; 382/141, 143, 144, 145, 147, 149, 151; 438/14; 324/762.01, 762.05; 356/237.4, 237.5
  See application file for complete search history.

(56) References Cited

U.S. PATENT DOCUMENTS 6,636,064 B1 * 10/2003 Satya et al. ................ 324/750.3
6,751,519 B1 *  6/2004 Satya et al. .................... 700/121
(Continued)

OTHER PUBLICATIONS

Bishop, Michael and David Joy. Feasibility Study for High Energy SEMBased Reference Measurement System for Litho Metrology. AIP Conference Proceedings. 2005. pp. 407-410. 788. American Institute of Physics. United States of America.
(Continued)

*Primary Examiner* — David A Vanore
(74) *Attorney, Agent, or Firm* — Suiter Swantz pc llo

(57) ABSTRACT

The present disclosure is directed to a method of performing SEM overlay metrology with scan direction substantially aligned with or parallel to feature placement or patterning of overlay target structures. By scanning target structures in the same or similar direction to the feature placement, blurring at the edges of interest is avoided and a line-to-line or edge-to-edge offset between pattern elements is less susceptible to error from blurring at scanned edges of interest. For example, at least two linear pattern elements corresponding to at least two sample layers may be scanned along or parallel to the direction of feature placement (i.e., along or parallel to long edges of the pattern elements).

25 Claims, 8 Drawing Sheets

(51) Int. Cl.
*H01L 21/66* (2006.01)
*G06T 7/00* (2006.01)

(56) References Cited

U.S. PATENT DOCUMENTS

| | | | |
|---|---|---|---|
| 7,065,737 B2 | 6/2006 | Phan et al. | |
| 7,080,330 B1 | 7/2006 | Choo et al. | |
| 7,166,838 B1* | 1/2007 | Janik | 250/310 |
| 7,218,399 B2 | 5/2007 | Hayano | |
| 7,241,991 B1* | 7/2007 | Standiford et al. | 250/306 |
| 7,244,932 B2 | 7/2007 | Hamashima et al. | |
| 7,372,016 B1* | 5/2008 | Tortonese et al. | 250/252.1 |
| 7,408,642 B1* | 8/2008 | DiBiase | 356/401 |
| 7,495,245 B2 | 2/2009 | Zani et al. | |
| 7,570,797 B1* | 8/2009 | Wang et al. | 382/145 |
| 7,570,800 B2* | 8/2009 | Lin et al. | 382/149 |
| 7,747,062 B2* | 6/2010 | Chen et al. | 382/145 |
| 7,847,939 B2 | 12/2010 | Ku et al. | |
| 7,879,627 B2* | 2/2011 | Ghinovker et al. | 438/14 |
| 7,987,057 B1* | 7/2011 | DiBiase | 702/59 |
| 8,010,307 B2 | 8/2011 | Fang et al. | |
| 8,041,103 B2* | 10/2011 | Kulkarni et al. | 382/144 |
| 8,245,161 B1* | 8/2012 | Tortonese et al. | 716/51 |
| 8,253,119 B1* | 8/2012 | Brodie et al. | 250/492.22 |
| 8,411,287 B2 | 4/2013 | Smilde et al. | |
| 8,774,359 B1* | 7/2014 | Zhuang et al. | 378/70 |
| 2006/0255272 A1* | 11/2006 | Nakayama et al. | 250/310 |
| 2011/0134419 A1 | 6/2011 | Fuchs et al. | |
| 2014/0319342 A1 | 10/2014 | Fan et al. | |
| 2014/0353498 A1* | 12/2014 | Shur | 250/307 |

OTHER PUBLICATIONS

Hotta, Shoji, Takumici Sutani, Scott Halle, Daniel Moore, Chas Archie, Akiyuki Sugiyama, Masahiko Ikeno, Atsuko Yamaguchi, and Kazuyoshi Torii. Critical Dimension Scanning Electron Microscope Local Overlay Measurement and Its Application for Double Patterning of Complex Shapes. Journal of Micro/Nanolithography, MEMS, and MOEMS. Apr.-Jun. 2011. vol. 10(2). Society of Photo-Optical Instrumentation Engineers (SPIE).

* cited by examiner

SYSTEM AND METHOD OF SEM OVERLAY METROLOGY

PRIORITY

The present application claims priority under 35 U.S.C. §119(e) to U.S. Provisional Patent Application Ser. No. 61/830,927, titled METHOD OF SEM OVERLAY METROLOGY, By Dmitry Shur, filed Jun. 4, 2013, or is an application of which currently co-pending application(s) are entitled to the benefit of the filing date. The above-referenced provisional patent application is hereby incorporated by reference in its entirety.

TECHNICAL FIELD

The present disclosure generally relates to the field of overlay metrology and, more particularly, to scanning electron microscopy (SEM) overlay metrology.

BACKGROUND

As semiconductor devices continue to be manufactured on smaller scales, the systems used to monitor and control fabrication parameters must provide higher accuracy measurements and operate within tighter error margins. Optical metrology systems are commonly used to measure overlay error between layers disposed upon a substrate, such as a semiconductor wafer. However, the industry is now utilizing scanning electron microscopy (SEM) systems as an alternative to the illumination-based systems in order to achieve higher levels of accuracy on the basis of a high resolution achievable by SEM.

One problem with SEM overlay metrology systems is that edge blurring can occur due to rather large e-beam spot diameter compared to pixel size at high SEM magnifications and e-beam interaction volume. It should be noted, that an interaction volume is of critical importance for SEM image. The information depth (depth from which secondaries are emitted) may reach several hundred of nanometers depending on primary electron energy, target material, pattern, etc. The secondary electron signal is displayed at the electron probe position rather than at the actual secondary electron production position. If the scanning electron probe (primary beam) passes an edge on top the patterned surface (as shown in FIG. 1) a diffusion contrast can be created. Detailed description can be found in classic SEM text books like those by A. Hessler-Wyser or Scanning Electron Microscopy by L. Reimer. This diffusion contrast leads to the edge broadening correlated with the scan direction. Such an edge broadening is a fundamental SEM artifact caused by the fact of sequential pixel by pixel image formation. In one aspect, this disclosure is directed (but not limited to) minimizing the effect of edge broadening/blurring on the overlay measured by SEM apparatus.

This edge blurring may have acute influence on precision, accuracy, tool matching, and other characteristics of the overlay measurement. Frame averaging and sophisticated edge detection algorithms may be used to reduce error from edge blurring; however, there is a need for advances in the art that may help to avoid SEM artifacts resulting from edge blurring (e.g., nuisance signals or imaging error due to electron collection at edges).

SUMMARY

In one aspect, this disclosure is directed to a method of performing SEM overlay metrology with scan direction substantially aligned with or parallel to feature placement or patterning of overlay target structures. Scanning in the same or similar direction to the pattern lines may avoid edge blurring caused by electron collection at scanned edge regions of interest. Because the scan is performed along or parallel to the edge regions of interest, any blurring will primarily occur at the edges that are non-essential to overlay determination. Edge blurring may occur, for example, at lower and upper edges for a horizontal (X-axis) target structure including linear pattern elements disposed in the vertical direction (i.e., features are placed along or parallel to the Y-axis). For an X-axis target structure, the line-to-line (X-axis offset) is substantially unaffected by blurring at the lower and upper edges so long as the side edges (i.e., those extending along or parallel to the Y-axis) are clearly resolved. The same is true for vertical target structures with linear pattern elements disposed in the horizontal direction. By scanning vertical (Y-axis) target structures in the same or similar direction to the horizontal feature placement, edge blurring at the lower and upper edges is avoided and line-to-line (Y-axis) offset between the linear pattern elements is less susceptible to error from blurring at scanned edges of interest.

In an embodiment, the method includes the steps of: scanning an electron beam across a surface of the sample in a scan direction that is substantially collinear or parallel to a first set of linear pattern elements, the first set of linear pattern elements including at least two linear pattern elements corresponding to the at least two layers of the sample (e.g., at least a first layer and a second layer formed on a substrate); detecting electrons from a scanned portion of the surface of the sample including the first set of linear pattern elements; and determining a spatial offset between the at least two linear pattern elements of the first set of linear pattern elements based upon the detected electrons.

In an embodiment, the method may be manifested by a system for performing overlay metrology, where the system includes: a stage configured to support a sample, the sample including a substrate with at least two layers formed thereon; an electron beam source configured to generate an electron beam, the electron beam source being further configured to scan the electron beam across a surface of the sample in a scan direction that is substantially collinear or parallel to a first set of linear pattern elements, the first set of linear pattern elements including at least two linear pattern elements corresponding to the at least two layers of the sample; at least one detector configured to detect electrons from a scanned portion of the surface of the sample including the first set of linear pattern elements; and a computing system in communication with the at least one detector, the computing system being configured to determine a spatial offset between the at least two linear pattern elements of the first set of linear pattern elements based upon the detected electrons.

Various embodiments of the system and method are described in further detail below with reference to illustrative drawings. Those skilled in the art will appreciate that the use of terms such as, but not limited to, "first," "second," "X-axis," and "Y-axis" are not intended to limit the present disclosure to a particular arrangement. Rather, the terms are illustrative of the relationship between feature placement/patterning and scan direction. It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1:
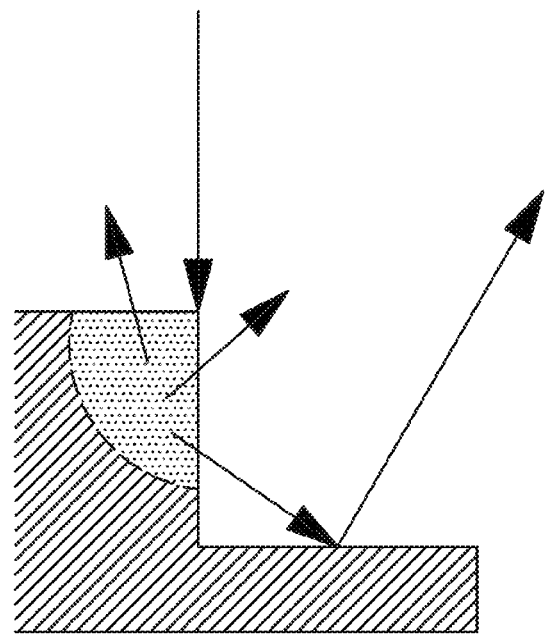
FIG. 1 illustrates a scanning electron probe (primary beam) passing an edge on top of a patterned surface, whereby a diffusion contrast may be created.
Figure 1:
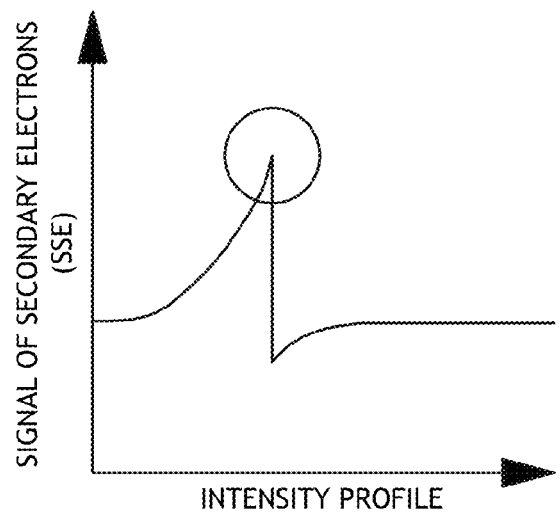
Figure 2:
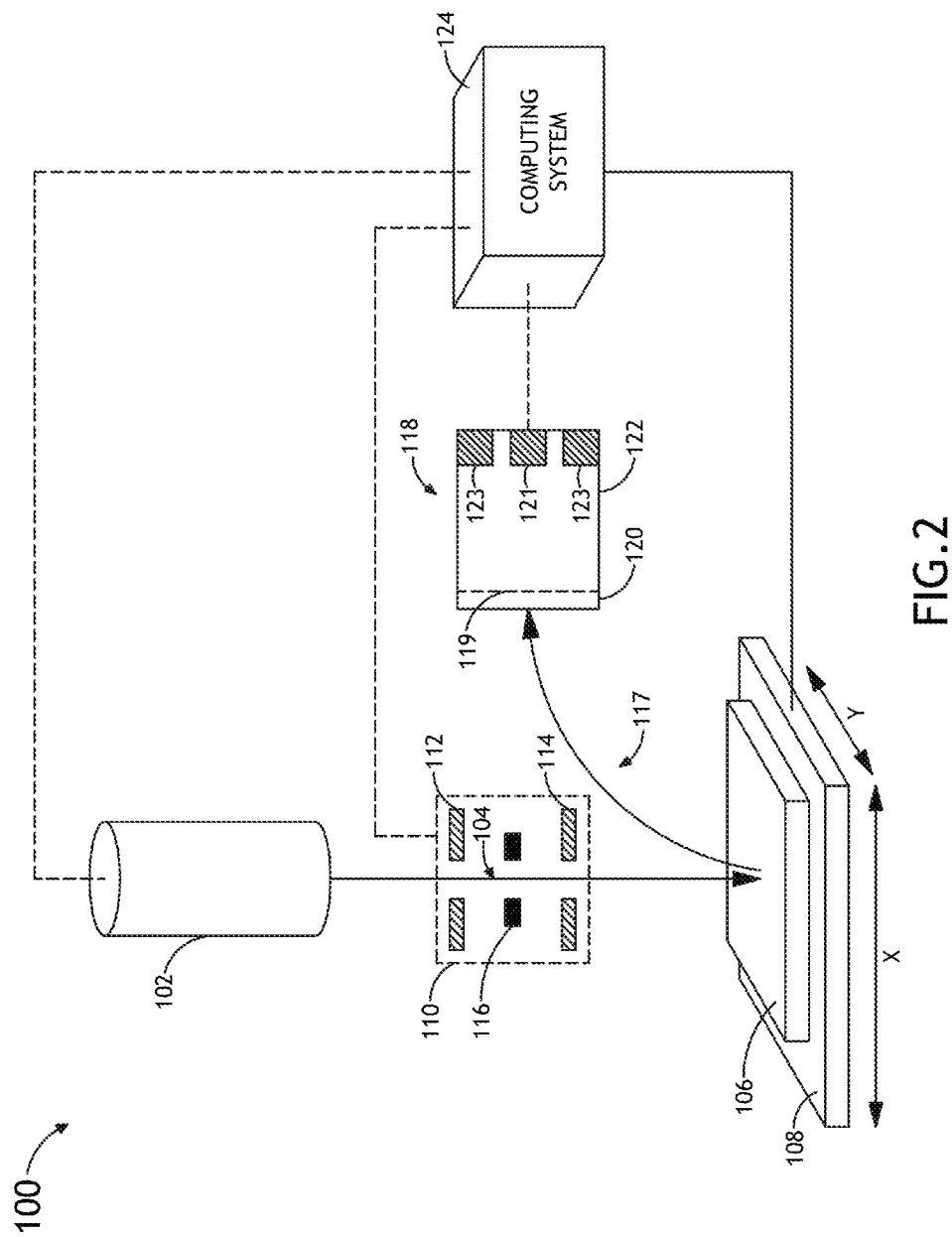
FIG. 2 is a block diagram illustrating a system for performing overlay metrology, in accordance with an embodiment of this disclosure.
Figure 3A:
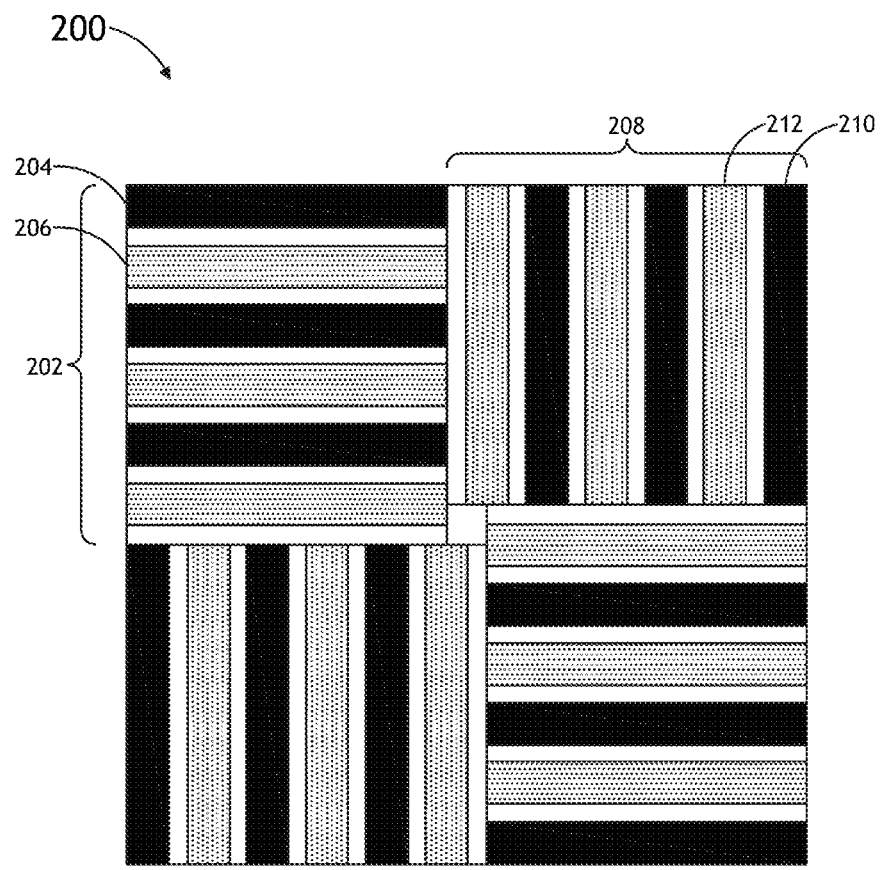
FIG. 3A is a conceptually illustration of an overlay metrology target, in accordance with an embodiment of this disclosure.
Figure 3B:
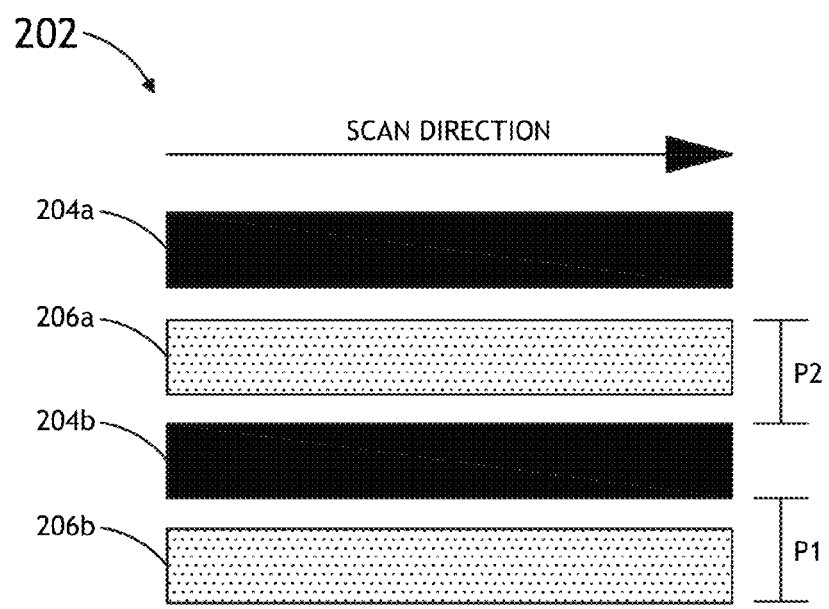
FIG. 3B is a conceptually illustration of a set of pattern elements with feature placement in a first direction, the set of pattern elements forming a portion of an overlay metrology target, in accordance with an embodiment of this disclosure.
Figure 3C:
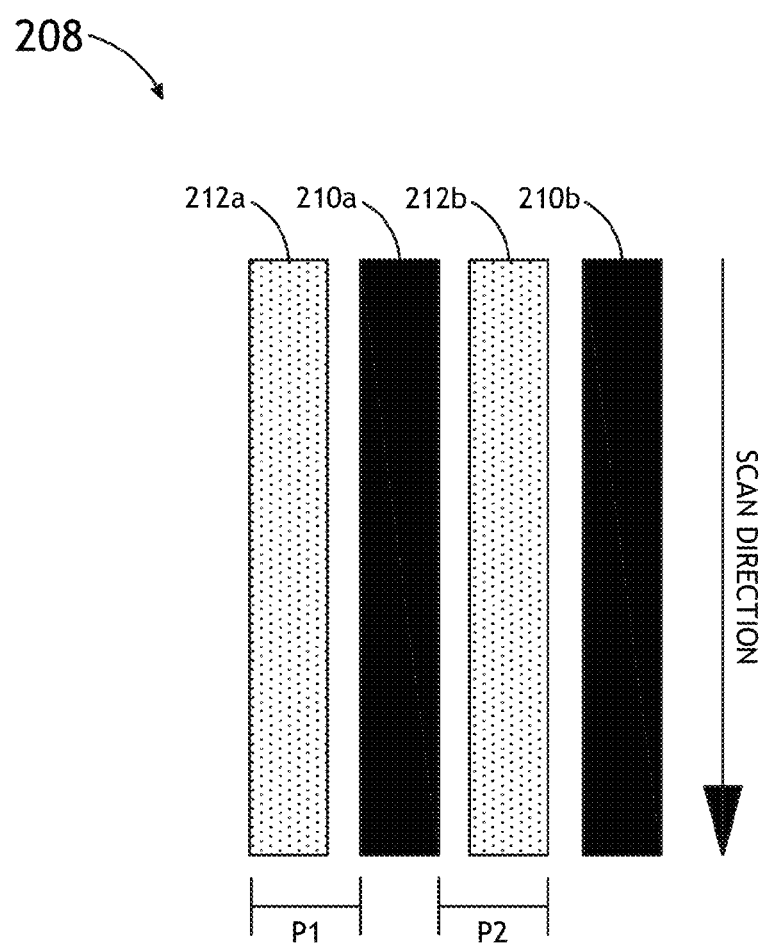
FIG. 3C is a conceptually illustration of a second set of pattern elements with feature placement in a second direction different from the first direction, the second set of pattern elements forming a portion of an overlay metrology target, in accordance with an embodiment of this disclosure.
Figure 3D:
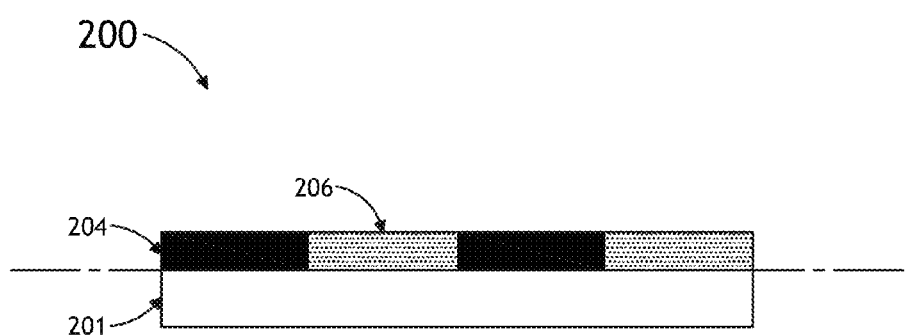
FIG. 3D is a conceptually illustration of a sample including a substrate with two or more layers formed thereon, where an overlay target formed on the substrate includes at least a first pattern element associated with a first sample layer and a second pattern element associated with a second sample layer, where the second pattern element(s) are at the same height (or same level) as the first pattern element(s), in accordance with an embodiment of this disclosure.
Figure 3E:
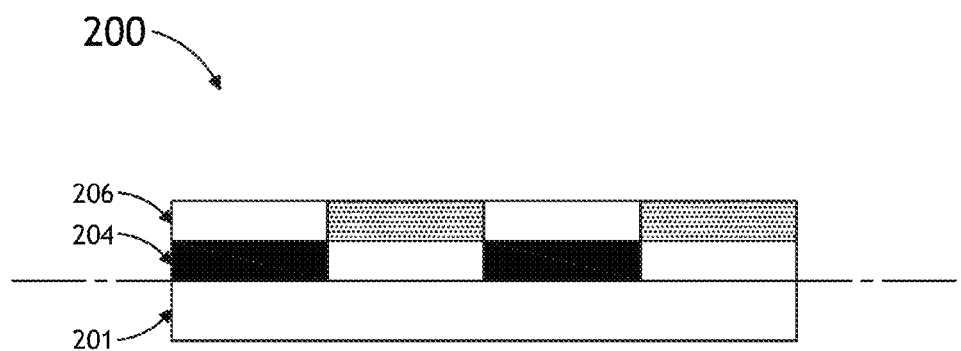
FIG. 3E is a conceptually illustration of a sample including a substrate with two or more layers formed thereon, where an overlay target formed on the substrate includes at least a first pattern element associated with a first sample layer and a second pattern element associated with a second sample layer, where the second pattern element(s) are stacked on top of the first pattern element(s), in accordance with an embodiment of this disclosure.
Figure 4:
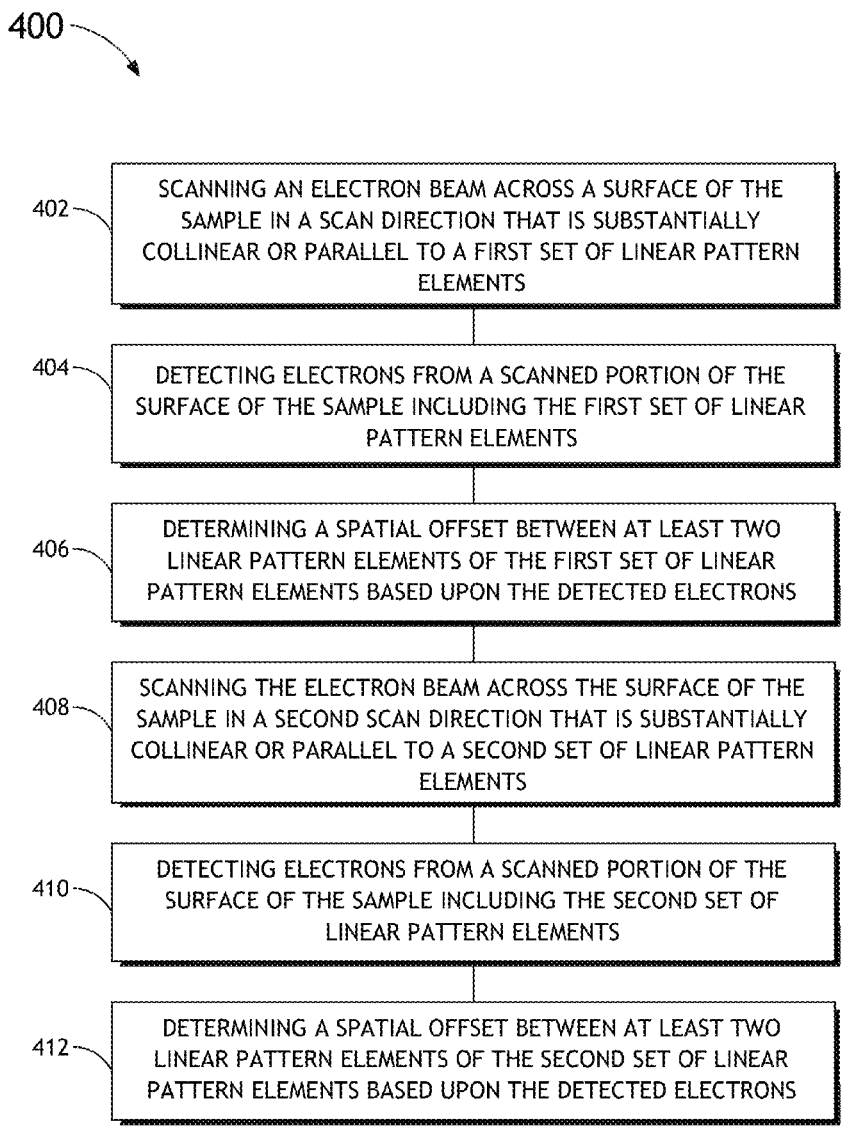
FIG. 4 is a flow diagram illustrating a method of performing overlay metrology, in accordance with an embodiment of this disclosure.

FIGS. 2 through 4 generally illustrate embodiments of a system and method for performing scanning electron microscopy (SEM) overlay metrology with scan direction substantially aligned with or parallel to feature placement or patterning of overlay target structures. Scanning in the same or similar direction to the pattern lines may avoid edge blurring caused by buildup of electrons, and as a result, oversampling at scanned edge regions of interest. Because the scan is performed along or parallel to the edge regions of interest, any blurring will primarily occur at the edges that are non-essential to overlay determination. For example, an (X-axis offset) overlay target structure with pattern lines formed along or parallel to the Y-axis may be scanned in alignment with or parallel to the Y-axis; while an (Y-axis offset) overlay target with pattern lines formed along or parallel to the X-axis may be scanned in alignment with or parallel to the X-axis. Scanning in the same or similar direction to feature placement/patterning may avoid blurring at the edges of interest (i.e., pattern element edges that are used in edge-to-edge or line-to-line spatial offset measurements).

Looking now to FIG. 2 a SEM overlay metrology system 100 is illustrated in accordance with an embodiment of this disclosure. In some embodiments, the system 100 may include, but is not limited to, a defect-review (DR) SEM tool with SEM overlay option, a critical-dimension (CD) SEM tool with SEM overlay option, a standalone SEM tool, a lithography/etch tool with integrated SEM overlay metrology, or a lithography/etch metrology cluster with features such as imaging optical overlay, scatterometry optical overlay, scatterometry CD, and CDSEM with SEM overlay option. The system 100 may be configured to scan a sample 106 such as, but not limited to, a wafer (e.g., semiconductor wafer) having two or more layers formed thereon with an electron beam 104 in order to determine overlay error (e.g., a misalignment or spatial offset between at least two layers of interest).

The system 100 may operate in any scanning mode known in the art. For example, the system 100 may operate in a swathing mode when scanning an electron beam 104 across the surface of the sample 106. In this regard, the system 100 may scan an electron beam 104 across the sample 106, while the sample is moving, with the direction of scanning being nominally perpendicular to the direction of the sample motion. By way of another example, the system 100 may operate in a step-and-scan mode when scanning an electron beam 104 across the surface of the sample 106. In this regard, the system 100 may scan an electron beam 104 across the sample 106, which is nominally stationary when the beam 104 is being scanned.

The system 100 may include an electron beam source 102 for generating one or more electron beams 104. The electron beam source 102 may include any electron source known in the art. For example, the electron beam source 102 may include, but is not limited to, one or more electron guns. In some embodiments, a computing system 124 or controller may be communicatively coupled to the electron beam source 102. The computing system 124 may be configured to adjust one or more electron source parameters via a control signal to the electron beam source 102. For example, the computing system 124 may be configured to vary the beam current for the electron beam 104 emitted by source 102 via a control signal transmitted to control circuitry of the electron beam source 102.

The sample 106 may be disposed on a sample stage 108 configured to support the sample 106 during scanning. In some embodiments, the sample stage 108 is an actuatable stage. For example, the sample stage 108 may include, but is not limited to, one or more translational stages suitable for selectably translating the sample 106 along one or more linear directions (e.g., x-direction, y-direction and/or z-direction). By way of another example, the sample stage 108 may include, but is not limited to, one or more rotational stages suitable for selectably rotating the sample 106 along a rotational direction. By way of another example, the sample stage 108 may include, but is not limited to, a rotational stage and a translational stage suitable for selectably translating the sample along a linear direction and/or rotating the sample 106 along a rotational direction.

In some embodiments, the computing system 124 or controller is communicatively coupled to the sample stage 108. The computing system 124 may be configured to adjust one or more stage parameters via a control signal transmitted to the sample stage 108. The computing system 124 may be configured to vary the sample scanning speed and/or control the scan direction via a control signal transmitted to control circuitry of the sample stage 108. For example, the computing system 124 may be configured to vary the speed and/or control the direction with which sample 106 is linearly translated (e.g., x-direction or y-direction) relative to the electron beam 104. As discussed in further detail below, the sample 106 may be scanned in the same or similar direction to feature placement (i.e., along or parallel to pattern lines) of target structures forming an overlay metrology target or mark on the sample 106.

The system 100 may further include a set of electron-optic elements 110. The set of electron-optics may include any electron-optic elements known in the art suitable for focusing and/or directing the electron beam 104 onto a selected portion of the sample 106. In one embodiment, the set of electron-optics elements includes one or more electron-optic lenses. For example, the electron-optic lenses may include, but are not limited to, one or more condenser lenses 112 for collecting electrons from the electron beam source. By way of another example, the electron-optic lenses may include, but are not limited to, one or more objective lenses 114 for focusing the electron beam 104 onto a selected region of the sample 106. In some embodiments, the electron beam 104 may be directed to the sample 106 at a controlled angle to the sample grating. Because wafer system of coordinates does not necessarily coincide with SEM system of coordinates, controlling a fine scan angle may improve matching between the coordinate systems and significantly contribute to sampling performance/accuracy.

In some embodiments, the set of electron-optics elements includes one or more electron beam scanning elements 116. For example, the one or more electron beam scanning elements 116 may include, but are not limited to, one or more scanning coils or deflectors suitable for controlling a position of the beam relative to the surface of the sample 106. In this regard, the one or more scanning elements 116 may be utilized to scan the electron beam 104 across the sample 106 in a selected scan direction or patter. For example, the sample 106 may be scanned in the same or similar direction to feature placement (i.e., along or parallel to pattern lines) of target structures forming an overlay metrology target or mark on the sample 106. The computing system 124 or controller may be communicatively coupled to one or more of the electron-optic elements 110, such as the one or more scanning elements 116. Accordingly, the computing system may be configured to adjust one or more electron-optic parameters and/or control the scan direction via a control signal transmitted to the one or more communicatively coupled electron-optic elements 110.

The system 100 may further include a detector assembly 118 configured to receive electrons 117 from the sample 106. In some embodiments, the detector assembly 118 includes an electron collector 120 (e.g., secondary electron collector). The detector assembly may further include an energy filter 119 based, for example, on retarding field principle. In this regard, the energy filter 119 may be configured to stop low energy secondaries while passing high energy secondaries (i.e., backscattered electrons). If the energy filter 119 is not activated, all secondary electrons are detected according to collection efficiency of the detection system. By subtracting high energy electron image from overall electron image, low energy secondary electron image can be obtained. The detector assembly 118 may further include a detector 122 (e.g., scintillating element and PMT detector 122) for detecting electrons from the sample surface (e.g., secondary electrons). In some embodiments, the detection system 122 may include several electron detectors, such as, for example, one or more Bright Field (BF) detectors 121 and one or more Dark Field (DF) detectors 123. In some embodiments, there may be from 2 to 8 (or even more) DF detectors 123. The BF detector 121 detects electrons with low (according to wafer normal) emission angles, while DF detectors 123 provide information carried by the electrons with higher emission angles. In some embodiments, the detector 122 of the detector assembly 118 includes a light detector. For example, the anode of a PMT detector of the detector 122 may include a phosphor anode, which is energized by the cascaded electrons of the PMT detector absorbed by the anode and may subsequently emit light. In turn, the light detector may collect light emitted by the phosphor anode in order to image the sample 106. The light detector may include any light detector known in the art, such as, but not limited to, a CCD detector or a CCD-TDI detector. The system 100 may include additional/alternative detector types such as, but not limited to, Everhart-Thornley type detectors. Moreover, the embodiments described herein are applicable to single detector and multiple-detector arrangements.

In some embodiments, the computing system 124 or controller is communicatively coupled to the detector assembly 118. The computing system 124 may be configured to adjust one or more image forming parameters via a control signal transmitted to the detector assembly 118. For example, the computing system may be configured to adjust the extraction voltage or the extraction field strength for the secondary electrons. Those skilled in the art will appreciate that "the computing system 124" may include one or more computing systems or controllers, such as one or more processors configured to execute one or more instruction sets embedded in program instructions stored by at least one non-transitory signal bearing medium. The computing system 124 may control various scanning or sampling parameters such as, but not limited to, those described in patent application Ser. No. 14/260,053 which is incorporated by reference in its entirety.

While the foregoing description focused on the detector assembly 118 in the context of the collection of secondary electrons, this should not be interpreted as a limitation on the present invention. It is recognized herein that the detector assembly 118 may include any device or combination of devices known in the art for characterizing a sample surface or bulk with an electron beam 104. For example, the detector assembly 118 may include any particle detector known in the art configured to collect backscattered electrons, Auger electrons, transmitted electrons or photons (e.g., x-rays emitted by surface in response to incident electrons). In some embodiments, as discussed above, the detected electrons are differentiated (e.g., secondary electrons vs. backscattered electrons) based upon the energy levels and/or emission angles of the detected electrons, and by subtracting high energy electron image from overall electron image, low energy secondary electron image can be obtained.

FIG. 3A illustrates an overlay target 200 that may be formed on a portion of the sample 106. For example, the overlay target 200 may include one or more target structures 202/208 including at least one pattern element 204/210 corresponding to a first layer formed on a sample substrate and at least one pattern element 206/212 corresponding to a second layer formed on the sample substrate. As shown in FIG. 3B, a target structure 202 may be suitable for overlay metrology in a first direction (e.g., for determination of Y-axis spatial offsets). For example, the target structure 202 may include one or more pattern elements 204 (e.g., pattern elements 204a and 204b) corresponding to a first layer of the sample 106 and one or more pattern elements 206 (e.g., pattern elements 206a and 206b) corresponding to a second layer of the sample 106, where the feature placement or patterning of the pattern elements 204 and 206 is substantially perpendicular to the first direction (e.g., extending along or parallel to the X-axis). To avoid or reduce blurring at the edges of interest, the system 100 may be configured to scan the pattern elements 204 and 206 in the same or similar direction to the feature placement or patterning (i.e., along or parallel to the X-axis). An overlay offset may be computed by comparing a first measured edge-to-edge distance (P1) and a second measured edge-to-edge distance (P2). For example, a spatial offset corresponding to an offset in the first direction between the first layer and the second layer may be determined according to the mathematical formula:

$$\frac{P1 - P2}{2}.$$

More sophisticated algorithms can be proposed especially if P1 and P2 are related to upper and lower layers (different heights).

FIG. 3C illustrates an embodiment of the target structure 208 suitable for overlay metrology in a second direction (e.g., for determination of X-axis spatial offsets). For example, the target structure 208 may include one or more pattern elements 210 (e.g., pattern elements 210a and 210b) corresponding to a first layer of the sample 106 and one or more pattern elements 212 (e.g., pattern elements 212a and 212b) corresponding to a second layer of the sample 106, where the feature placement or patterning of the pattern elements 210 and 212 is substantially perpendicular to the first direction (e.g., extending along or parallel to the Y-axis). To avoid or reduce blurring at the edges of interest, the system 100 may be configured to scan the pattern elements 210 and 212 in the same or similar direction to the feature placement or patterning (i.e., along or parallel to the Y-axis). In a similar manner to that described with regard to target structure 202, an overlay offset may be computed by comparing a first measured edge-to-edge distance (P1) and a second measured edge-to-edge distance (P2).

Those skilled in the art will appreciate that additional/alternative target structures may be formed and that the foregoing embodiments are not intended as limits on the present disclosure. In general, the system 100 may be configured to scan any set of pattern elements including at least one pattern element corresponding to a first sample layer and at least one pattern element corresponding to a second sample layer, where the scan direction is substantially collinear or parallel to the feature placement or pattern lines and/or where the scan direction is substantially perpendicular to the direction of the overlay offset being measured.

In some embodiments, the system 100 is further configured to scan the one or more pattern elements 204/210 corresponding to the first sample layer according to a first established set of scan parameters and the one or more pattern elements 206/212 corresponding to the second sample layer according to a second established set of scan parameters. For example, the computing system 124 may be configured to establish and/or store pre-determined scan parameters for "double grab" sampling. In some embodiments, as shown in FIG. 3E, a first set of pattern elements 204 may be formed in a first layer disposed upon a substrate 201, and a second set of pattern elements 206 may be formed in a second layer that is stacked on top of the first layer. This is in alternative to embodiments (as illustrated in FIG. 3D) were the first set of pattern elements 204 and the second set of pattern elements 206 are formed at the same level/height. The computing system 124 may be configured to control scanning parameters according to an established scan recipe. In some embodiments, a respective scan recipe may be established for each of the first (lower) and second (upper) layers.

By way of example, where the first set of pattern elements 204 and the second set of pattern elements 206 are formed at the same level (as shown in FIG. 3D), a "single grab" detection mode may be utilized with the detection system tuned for sensitivity to low energy secondaries and/or low emission angle secondaries. By way of another example, where the first set of pattern elements 204 and the second set of pattern elements 206 are formed at different levels/heights (as shown in FIG. 3E), a single grab or double grab detection mode may be utilized. In embodiments where a single grab detection mode is utilized, the detection system may be tuned for sensitivity to low energy secondaries, high energy secondaries, and low emission angle secondaries. In embodiments where a double grab detection mode is utilized, a first grab tuning may be set for sensitivity to low energy and low emission angle secondaries, while a second grab tuning may be set for high energy and low emission angle secondaries. It is noted that the foregoing examples are provided for illustrative purposes and that other tuning parameters or detection modes may be exercised without departing from the scope of this disclosure.

A method 400 of performing SEM overlay metrology is illustrated in FIG. 4 in accordance with an embodiment of this disclosure. The Method 400 may be manifested by system 100, and as such, may include one or more steps or operations for carrying functions described with regard to the foregoing embodiments of system 100. In some embodiments, a non-transitory carrier medium may include program instructions causing the computer system 124 to perform the steps or operations of method 400. It is noted, however, that the method 400 is not limited to the foregoing embodiments and may be manifested by any SEM-based system suitable for carrying out the following steps. The method 400 may be performed on a sample 106 including an overlay target 200 as described above.

At step 402, an electron beam 104 may be scanned across a surface of the sample 106 in a scan direction that is substantially collinear or parallel to a first set of linear pattern elements 202 (e.g., in the same or similar direction to linearly placed target features). At step 404, a detector assembly 118 may receive electrons from the surface of the sample 106 in order to image at least one pattern element 204 corresponding to a first layer of the sample 106 and at least one pattern element 206 corresponding to a second layer of the sample 106. At step 406, edge-to-edge or line-to-line measurements are performed to determine a spatial offset between the first layer and the second layer, wherein the determined offset is in a direction that is substantially perpendicular to the scan direction.

In some embodiments, the system further includes steps 408 through 412 for measuring at least one additional set of linear pattern elements 208 suitable for determining overlay error in a second direction (e.g., a second direction that is substantially perpendicular to the direction of the first determined spatial offset). At step 408, an electron beam 104 may be scanned across a surface of the sample 106 in a second scan direction that is substantially collinear or parallel to the second set of linear pattern elements 208. At step 410, the detector assembly 118 may receive electrons from the surface of the sample 106 in order to image at least one pattern element 210 corresponding to the first layer of the sample 106 and at least one pattern element 212 corresponding to the second layer of the sample 106. At step 412, edge-to-edge or line-to-line measurements are performed to determine a spatial offset between the first layer and the second layer, wherein the determined offset is in a direction that is substantially perpendicular to the second scan direction.

Accordingly, the determined overlay error may include offsets in a first direction (e.g., X-axis offset) and a second direction (e.g., Y-axis offset), where edge blurring is avoided by scanning the first direction (X-axis) target structures in a first perpendicular scan direction (e.g., along or parallel to the Y-axis) and second direction (Y-axis) target structures in a second perpendicular scan direction (e.g., along or parallel to the X-axis), respectively. By scanning the target structures in the same or similar direction to feature placement or pattern lines, the system 100 and method 400 described herein may allow for improvements in precision and accuracy of SEM overlay measurements, tool matching of SEM overlay tools, and tolerance of tool induced shift (TIS) of SEM overlay tools.

Those having skill in the art will appreciate that there are various vehicles by which processes and/or systems and/or other technologies described herein can be embodied (e.g., hardware, software, and/or firmware), and that the preferred vehicle will vary with the context in which the processes and/or systems and/or other technologies are deployed. In some embodiments, various steps, functions, and/or operations are carried out by one or more of the following: electronic circuits, logic gates, multiplexers, programmable logic devices, ASICs, analog or digital controls/switches, microcontrollers, or computing systems. A computing system may include, but is not limited to, a personal computing system, mainframe computing system, workstation, image computer, parallel processor, or any other device known in the art. In general, the terms "computing system" and "controller" are broadly defined to encompass any device having one or more processors, which execute instructions from a carrier medium. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A method of performing overlay metrology upon a sample including a substrate with at least two layers formed thereon, the method comprising:
   scanning an electron beam across a surface of the sample in a scan direction that is substantially collinear or parallel to a first set of linear pattern elements, the first set of linear pattern elements including at least two linear pattern elements corresponding to the at least two layers of the sample;
   detecting electrons from a scanned portion of the surface of the sample including the first set of linear pattern elements; and
   determining a spatial offset between the at least two linear pattern elements of the first set of linear pattern elements based upon the detected electrons.

2. The method of claim 1, wherein the determined spatial offset between the at least two linear pattern elements of the first set of linear pattern elements comprises an offset in a direction that is different from the scan direction.

3. The method of claim 2, wherein the direction of the determined spatial offset between the at least two linear pattern elements of the first set of linear pattern elements is substantially perpendicular to the scan direction.

4. The method of claim 1, further comprising:
   scanning the electron beam across the surface of the sample in a second scan direction that is substantially collinear or parallel to a second set of linear pattern elements, the second set of linear pattern elements including at least two linear pattern elements corresponding to the at least two layers of the sample;
   detecting electrons from a scanned portion of the surface of the sample including the second set of linear pattern elements; and
   determining a spatial offset between the at least two linear pattern elements of the second set of linear pattern elements based upon the detected electrons.

5. The method of claim 4, wherein the determined spatial offset between the at least two linear pattern elements of the second set of linear pattern elements comprises an offset in a direction that is different from the second scan direction.

6. The method of claim 5, wherein the direction of the determined spatial offset between the at least two linear pattern elements of the second set of linear pattern elements is substantially perpendicular to the second scan direction.

7. The method of claim 4, wherein the first scan direction is different from the second scan direction.

8. The method of claim 7, wherein the first scan direction is substantially perpendicular to the second scan direction.

9. The method of claim 1, further comprising:
   differentiating secondary electrons based upon respective energy levels or emission angles of the detected electrons.

10. The method of claim 1, further comprising:
    differentiating secondary electrons from backscattered electrons based upon energy levels of the detected electrons.

11. The method of claim 1, further comprising:
    differentiating backscattered electrons based upon respective energy levels or emission angles of the detected electrons.

12. The method of claim 1, further comprising:
    establishing a first set of scan parameters for one or more pattern elements corresponding to a first layer of the sample;
    establishing a second set of scan parameters for one or more pattern elements corresponding to a second layer of the sample; and
    scanning each of the at least two pattern elements corresponding to the at least two layers of the sample, respectively, according to the established scan parameters.

13. The method of claim 1, further comprising:
tuning a detector assembly to increase sensitivity to low energy electrons and low emission angle electrons when the at least two linear pattern elements are formed at the same height or level.

14. The method of claim 1, further comprising:
tuning a detector assembly to increase sensitivity to low energy electrons, high energy electrons, and low emission angle electrons when the at least two linear pattern elements are formed at different heights or levels.

15. The method of claim 1, further comprising:
when the at least two linear pattern elements are formed at different heights or levels, tuning a detector assembly to increase sensitivity, during a first grab, to low energy electrons and low emission angle electrons; and
tuning the detector assembly to increase sensitivity, during a second grab, to high energy electrons and low emission angle electrons.

16. A system for performing overlay metrology, comprising:
a stage configured to support a sample, the sample including a substrate with at least two layers formed thereon;
an electron beam source configured to generate an electron beam, the electron beam source being further configured to scan the electron beam across a surface of the sample in a scan direction that is substantially collinear or parallel to a first set of linear pattern elements, the first set of linear pattern elements including at least two linear pattern elements corresponding to the at least two layers of the sample;
at least one detector configured to detect electrons from a scanned portion of the surface of the sample including the first set of linear pattern elements; and
a computing system in communication with the at least one detector, the computing system being configured to determine a spatial offset between the at least two linear pattern elements of the first set of linear pattern elements based upon the detected electrons.

17. The system of claim 16, wherein the determined spatial offset between the at least two linear pattern elements of the first set of linear pattern elements comprises an offset in a direction that is different from the scan direction.

18. The system of claim 17, wherein the direction of the determined spatial offset between the at least two linear pattern elements of the first set of linear pattern elements is substantially perpendicular to the scan direction.

19. The system of claim 16, wherein the electron beam source is further configured to scan the electron beam across the surface of the sample in a second scan direction that is substantially collinear or parallel to a second set of linear pattern elements, the second set of linear pattern elements including at least two linear pattern elements corresponding to the at least two layers of the sample;
the at least one detector is further configured to detect electrons from a scanned portion of the surface of the sample including the second set of linear pattern elements; and
the computing system is further configured to determine a spatial offset between the at least two linear pattern elements of the second set of linear pattern elements based upon the detected electrons.

20. The system of claim 19, wherein the determined spatial offset between the at least two linear pattern elements of the second set of linear pattern elements comprises an offset in a direction that is different from the second scan direction.

21. The system of claim 20, wherein the direction of the determined spatial offset between the at least two linear pattern elements of the second set of linear pattern elements is substantially perpendicular to the second scan direction.

22. The system of claim 19, wherein the first scan direction is different from the second scan direction.

23. The system of claim 22, wherein the first scan direction is substantially perpendicular to the second scan direction.

24. The system of claim 16, wherein the computing system is further configured to differentiate secondary electrons from back-scattered electrons based upon respective energy levels or emission angles of the detected electrons.

25. The system of claim 16, wherein the computing system is further configured to:
store a first set of scan parameters for one or more pattern elements corresponding to a first layer of the sample; and
store a second set of scan parameters for one or more pattern elements corresponding to a second layer of the sample, wherein the at least two pattern elements corresponding to the at least two layers of the sample are scanned according to the stored scan parameters.

* * * * *